(12) United States Patent
Bischoff et al.

(10) Patent No.: US 12,251,339 B2
(45) Date of Patent: Mar. 18, 2025

(54) PRODUCING CUTS IN THE INTERIOR OF THE EYE (71) Applicant: Carl Zeiss Meditec AG, Jena (DE)

(72) Inventors: Mark Bischoff, Jena (DE); Gregor Stobrawa, Jena (DE); Dieter Grebner, Großlöbichau (DE)

(73) Assignee: Carl Zeiss Meditec AG, Jena (DE)

( * ) Notice: Subject to any disclaimer, the term of this patent is extended or adjusted under 35 U.S.C. 154(b) by 781 days.

(21) Appl. No.: 17/278,312

(22) PCT Filed: Sep. 11, 2019

(86) PCT No.: PCT/EP2019/074242
§ 371 (c)(1),
(2) Date: Mar. 21, 2021

(87) PCT Pub. No.: WO2020/058064
PCT Pub. Date: Mar. 26, 2020

(65) Prior Publication Data
US 2021/0330501 A1    Oct. 28, 2021

(30) Foreign Application Priority Data

Sep. 20, 2018  (DE) .................... 10 2018 007 573.8

(51) Int. Cl.
*A61F 9/008*    (2006.01)
(52) U.S. Cl.
CPC ....... *A61F 9/00836* (2013.01); *A61F 2009/00844* (2013.01); *A61F 2009/00872* (2013.01)
(58) Field of Classification Search
None
See application file for complete search history.

(56) References Cited

U.S. PATENT DOCUMENTS

| 2005/0251114 A1* | 11/2005 | Muhlhoff ............... A61F 9/008 606/4 |
| 2012/0078240 A1 | 3/2012 | Spooner |

(Continued)

FOREIGN PATENT DOCUMENTS

| DE | 199 40 712 A1 | 3/2001 |
| DE | 10 2005 013 949 A1 | 9/2006 |

(Continued)

OTHER PUBLICATIONS

English translation of IPRP for PCT International Application No. PCT/EP2019/074242, mailed Apr. 1, 2021, 8 pages.

(Continued)

*Primary Examiner* — Lynsey C Eiseman
*Assistant Examiner* — James Moss
(74) *Attorney, Agent, or Firm* — DeWitt LLP (57) ABSTRACT

An apparatus for producing incisions in an interior of an eye. For example, the apparatus includes an image recording device that records at least part of the image field and an image evaluation device that evaluates recordings of the image recording device and produces signals for the control device and/or the operator. Furthermore, the invention relates to a method for producing incisions in the interior of an eye, wherein an image recording device is used to record at least part of the image field and an image evaluation device evaluates the recordings of the image recording device and produces signals for the control device and/or the operator.

12 Claims, 2 Drawing Sheets

(56) References Cited

U.S. PATENT DOCUMENTS

| | | | |
|---|---|---|---|
| 2014/0128821 A1 | 5/2014 | Gooding et al. | |
| 2015/0190278 A1* | 7/2015 | Gooding | A61F 9/009 606/4 |
| 2016/0106582 A1* | 4/2016 | Campos | A61F 9/009 606/4 |
| 2018/0000641 A1* | 1/2018 | Rathjen | A61B 3/113 |

FOREIGN PATENT DOCUMENTS

| | | |
|---|---|---|
| DE | 10 2016 204 496 | 9/2017 |
| WO | WO 2004/105660 A1 | 12/2004 |
| WO | WO 2004/105661 A1 | 12/2004 |
| WO | WO 2005/048895 A1 | 6/2005 |
| WO | WO 2007/022993 A2 | 3/2007 |
| WO | WO 2008/055697 A1 | 5/2008 |
| WO | WO 2008/055705 A1 | 5/2008 |
| WO | WO 2008/055706 A1 | 5/2008 |
| WO | WO 2008/131878 A1 | 11/2008 |
| WO | WO 2016/061552 A1 | 4/2016 |

OTHER PUBLICATIONS

International Search Report for PCT/EP2019/074242, mailed Sep. 11, 2019, 5 pages.
English translation of International Search Report for PCT/EP2019/074242, mailed November Sep. 11, 2019, 3 pages.

* cited by examiner

PRODUCING CUTS IN THE INTERIOR OF THE EYE

RELATED APPLICATIONS

This application is a National Phase entry of PCT Application No. PCT/EP2019/074242 filed Sep. 11, 2019, which application claims the benefit of priority to DE Application No. 10 2018 007 573.8 filed, Sep. 20, 2018, the entire disclosures of which are incorporated herein by reference.

TECHNICAL FIELD

The invention relates to an apparatus for producing incisions in the interior of an eye, comprising a laser beam source embodied to emit pulsed laser radiation at a wavelength that penetrates into the cornea of the eye, a beam shaping device which comprises a beam optical unit which focuses the pulsed laser radiation into the interior of the eye at a focus and a beam deflection device, which displaces a focus of the radiation, wherein a control device is provided, the latter being embodied to control the laser beam source and the beam shaping device in order to produce at least one cut surface in the interior of the eye.

The invention further relates to a method for generating incisions in the interior of an eye, wherein at least one cut surface is defined in the interior of the eye and the cut surface is produced by the emission of pulsed laser radiation, wherein use is made of pulsed laser radiation at a wavelength that penetrates into the cornea and a focus of the laser radiation is displaced in the interior of the eye.

BACKGROUND

The shape of the front surface of the cornea is important for the imaging properties of the eye. For a refractive error correction, the practice of altering the cornea with the object of modifying the front surface of the cornea and hence the refractive properties thereof, and thus compensating the refractive error, has long been known. To this end, surgical methods were developed in the prior art, which cut a flap on the cornea, fold back said flap and then ablate material from the interior of the cornea exposed thus. Subsequently, the flap is folded back and the cornea has a differently shaped front surface on account of the material ablation. This correction principle is abbreviated LASIK, inter alia, in the prior art. Such methods will be referred to as hinged-flap refractive error correction below. In early embodiments, the flap was released by application of a mechanical keratome. The cornea is pressed flat by a planar contact glass and an incision producing the flap is implemented by use of the mechanical keratome. In a development, so-called laser keratomes are now used. In this respect, a laser keratome by Ziemer Ophthalmic Systems AG, Port, Switzerland, inter alia, is known. In respect of its beam deflection, it is embodied to produce the flap to be folded back. The first laser keratome was developed by Intralase Inc., USA, which now belongs to Abbott Laboratories, Illinois, USA. Both laser keratomes operate with pulsed laser radiation, with repetition rates and pulse energies differing.

The surgical refractive error correction was developed further into methods which isolate and extract material in the cornea. The material usually has the shape of a lenticule, which is why these methods are referred to here as lenticule-extracting methods or apparatuses. For the sake of clarity, the volume to be isolated and extracted is also referred to as "lenticule" even if a non-lenticular volume should be isolated and extracted in certain applications.

The apparatuses and methods specified at the outset relate to the principle of lenticule extraction. The lenticule-extracting apparatuses and methods are advantageous in that the front surface of the cornea is injured in a very much smaller region. There no longer is the need for a virtually complete ring-shaped incision on the corneal front surface, as is required to release a flap that exposes the interior of the cornea. Rather, a small incision at the edge which leads to the volume to be isolated and through which the isolated volume can be removed, possibly after a preceding comminution of the isolated material, is sufficient. However, the principle of lenticule extraction requires highly precise production of the cut surfaces in the interior of the cornea that isolate the lenticule. Further, to bring about the refractive error correction, at least one of the cut surfaces delimiting the lenticule should be located at a non-constant distance from the front surface of the cornea for the purposes of the smallest possible tissue consumption. Here, too, there is a difference to the approach which releases and folds-back a corneal flap since, in that case, there are no problems associated with locating the only cut surface, which produces the flap, at a constant distance from the front surface of the cornea, i.e., parallel to the front surface of the cornea. If the front surface of the cornea is pressed flat using a planar contact glass during the flap-producing incision, it is only necessary to produce one cut surface which, apart from the edge portions, is located parallel to the surface of the contact glass and which is also flat.

The fundamentals of lenticule-extraction refractive error correction are described in WO 2004/105660 and WO 2004/105661. Moreover, developments are known in the prior art. Thus, WO 2005/011547 discloses the use of contour lines as focused trajectories for fast lenticule isolation and WO 2008/055697 specifies calculation rules for how the boundaries of the lenticule, i.e., the cut surfaces to be produced, can be chosen. In particular, this document has disclosed the division of the cut surfaces delimiting the lenticule into an anterior flap surface, which is located at a constant distance from the front surface of the cornea, and a posterior lenticule surface, which is not located at a constant distance from the front surface of the cornea. The distance of the surfaces from one another, and hence their shape, influences the curvature of the cornea following the correction.

WO 2008/055705 and WO 2008/055706 consider the problem of the field curvature when using a non-planar contact glass and the generation of control data for the surgical method.

The cut surface is usually produced by pulsed laser radiation. Here, the targets of the laser radiation are arranged along a trajectory which is located in the cut surface and ultimately specifies the cut surface. WO 2008/055698 describes the arrangement of the targets along the trajectory, wherein provision is made of not also specifying a target for each laser radiation pulse emitted into the cornea.

WO 2008/131878 considers the question of how, following a termination or completion of a laser-surgical intervention, a further treatment which takes account of incisions already present in the cornea can be implemented.

WO 2007/022993 describes a contact glass which can be fastened to the cornea or the sclera of the eye using negative pressure. This serves to ensure a fixed coordinate relationship between the treatment laser and the eye and, in the process, prevent the eye from moving, which would undo this assignment again. For patient safety, a force sensor is often provided, the latter preventing the contact glass from damaging the eye when the patient moves (e.g., WO 2005/048895).

The prior art includes the VisuMax® femtosecond laser keratome by Carl Zeiss Meditec AG for the lenticule-extracting method. It uses a femtosecond fiber laser which emits in the infrared spectral range and which outputs laser pulses with a pulse repetition rate of 500 kHz, said laser pulses being focused into the cornea.

Furthermore, the production of incisions in the interior of the eye, for example the lens, the vitreous humor or the retina, using an fs laser is known (e.g., DE 199 40 712), which is used in so-called fs cataract treatment, for example.

It is conventional in known systems for producing incisions in the eye for the operator (physician) to visually monitor the progress of the intervention, either using a surgical microscope for co-observation or by way of a device made of camera and screen (both are described in DE 10 2005 013 949).

The time duration of the cut surface production is very important, both in respect of the quality of a refractive error correction and in respect of the acceptance by patients. With the duration of the intervention, the risk of bothersome eye movements increases; this can reduce the accuracy of the cut surface production or can even lead to it no longer being possible to produce a contiguous cut surface and the procedure having to be terminated. Additionally, a longer intervention is an undesirable burden for the patient. By contrast, the exact positioning of the cut surfaces in the cornea is very important for the quality of the result of the lenticule-extracting vision correction. Since the cut surface is produced by adjusting the focal position (focus) of the pulsed laser radiation along a trajectory, the positioning accuracy of the focus within the interior of the eye is ultimately important.

DE 10 2013 204 496 by the applicant has therefore disclosed a system which attains a fast cut surface production with high precision at the same time.

As a result, it is possible, for example, to carry out in a few seconds (about 5 s) laser therapy that was previously carried out in 30 s. This significantly increases the demands on the observation skills and the reaction speed of the operator. As a result, this can increase certain therapy risks for the patient in comparison with the current therapy standard.

The following are known support solutions for the operator:
  recording the video signal of the camera during the laser therapy (video log),
  recording control signals about the progress of the laser therapy (e.g., scanner log, energy log),
  automated control of the contact force between patient's eye and contact glass on the basis of the measured value of the contact force,
  automated workflow for continuing or resuming a laser therapy,
  producing an automatically generated document (treatment report), which summarizes essential treatment parameters and the treatment progress achieved for the operator.

It is prior art for the operator to have the task of initiating the treatment and tracking the treatment progress and, where necessary, initiating a termination of the treatment if they consider this right. For this purpose, they assess large amounts of information which they predominantly obtain from the visual observation of the treatment progress in the eyepiece of the co-observation microscope or by way of a screen display. By way of example, if the vacuum fixation of the patient's eye from the contact glass (or the patient interface) is released ("suction loss"), the operator stops the laser therapy, for example by operating a foot switch. The effectiveness of this manual monitoring function is of significant importance for patient safety.

A faster course of the laser therapy reduces the frequency of disruptions by disadvantageous events (e.g., patient activity, eye movement). However, at the same time there is an increased effect on the patient in the case of a disruption because a greater and frequently disadvantageous processing effect is attained between the time of the occurrence of the disruption and the introduction of an effective countermeasure (reaction time) by the operator. Hence, there is a risk of a significant endangerment of or injury to the patient in the case of a disruption during the course of the treatment.

In this context, the loss or reduction of the vacuum fixation of the patient's eye ("suction loss") was found to be particularly critical since, as a result, there is the risk of the eye moving in relation to the optical axis of the treatment device and hence the intended incision being interrupted and/or being continued/carried out at the wrong position. WO 2016/148 754 therefore proposes to monitor the negative pressure of the fixation using a second additional pressure sensor.

SUMMARY OF THE INVENTION

A benefit of embodiments of the invention lies in improving the monitoring of a laser treatment on the eye.

According to embodiments of the invention, this benefit is achieved by an apparatus for producing incisions in the interior of an eye, comprising
  a laser beam source embodied to emit pulsed laser radiation in the femtosecond range,
  a beam optical unit which has an image field and which focuses the pulsed laser radiation into the interior of the eye at a focus located within the image field,
  a beam deflection device, which displaces the focus within the image field,
  a control device embodied to control the laser beam source and the beam shaping device in order to produce at least one incision in the interior of the eye by specifying the trajectory,
  an image recording device embodied to record at least part of the image field,
  an image evaluation device embodied to evaluate recordings of the image recording device and produce signals for the control device and/or the operator.

According to embodiments of the invention benefits are achieved by a method for producing incisions in the interior of an eye, wherein
  at least one cut surface is defined in the interior of the eye,
  a trajectory located in the cut surface is defined,
  pulsed laser radiation in the femtosecond range at a wavelength penetrating the cornea is emitted into the interior of the eye,
  a beam optical unit is used, which has an image field and which focuses the pulsed laser radiation into the interior of the eye at a focus located within the image field,
  the focus is displaced in the interior of the eye and within the image field,
  an image recording device is used to record at least part of the image field,
  an image evaluation device evaluates recordings of the image recording device and produces signals for the control device and/or the operator.

Here, for example the laser beam source emits pulsed laser radiation with a pulse frequency of 1.2 MHz to 10 MHz.

Furthermore, for example the pulse energy is between 1 nJ and 200 nJ.

For example, the beam shaping device focuses the focus in such a way that it is located within the image field and has a maximum diameter of less than 3 µm.

An example wavelength lies in the range of 1030-1060 nm.

The aforementioned laser parameters are for example chosen in such a way that there is not only a material change but that the material change is also optically detectable, at least immediately after processing. Here, it is particularly preferable, for example, for the parameters to be chosen in such a way that the interaction of the laser radiation with the tissue brings about a bubble formation, as a result of which a bubble structure becomes observable.

The image evaluation device for example evaluates the images from the image recording device by image recognition or image measurement. This can be based on target images, for example of the planned treatment progress. As an alternative thereto, or in parallel therewith, optically detectable events of the incision production can be recognized or measured in order to recognize possible deviations from the intended progress.

The solution of the problem according to example embodiments of the invention thus consists in machine-based assistance for the user when monitoring the course of the treatment. In this case, the degree of assistance can go up to fully automated monitoring of the course of the treatment. In the best case, the only remaining task for the operator is that of starting and monitoring the automated course of the treatment.

Here, the invention offers the following options:
1. automated image recognition function in the video (machine monitoring by image processing) in respect of regularity of the treatment and automatic interruption of the treatment in the case of a recognized disruption,
2. automated measuring function (machine monitoring by signal monitoring) in respect of regularity of the treatment and automatic interruption of the treatment in the case of a recognized disruption,
3. option for the operator to continue an automatically interrupted treatment, i.e., deliberately override the automated monitoring function, to ignore the recommendations thereof or to correct or overwrite the measures thereof.

To this end, the image evaluation device requires specific functions. These are functions for digital image processing, which serve to make an assessment about the correctness of the treatment. A treatment is referred to as correct if the incisions produced arise where they should arise according to the planning that has been carried out by the operator with machine assistance. To this end, the image evaluation device uses image processing algorithms (e.g., edge filter, Hough transform, smoothing filter, contrast enhancement, brightness change, Fourier filter, difference images, image correlation, segmentation, calculation of the optical flow, etc.). In the simplest case, the assessment of the correctness is implemented by the comparison of actual measured image parameters with predefined target image parameters.

In n example variant, the image capture system is connected to a video capture system which allows the observation of the treatment progress after completion of the laser therapy but before the lenticule removal.

In the process, the video capture system (e.g., digital video recorder) facilitates the visualization of the treatment process with the same, increased or reduced speed of the image reproduction in comparison with the previous image recording. By reducing the speed of the image reproduction, the course of the laser therapy becomes more easily observable again for the operator (physician) and they can react to the observed course of the laser therapy during the subsequent step of lenticule removal. In the process, the described techniques of image processing can be used and further work steps for the lenticule removal can be derived.

By way of example, it is thus possible to recognize regions with a lack of bubble structure which preclude a subsequent lenticule separation; as a result, injury to the patient is avoided.

In another case, the operator can be informed about regions with a deviating bubble structure, which lead to the expectation of less easily separable tissue regions. They can then react to this by adapting their manual surgery technique, as a result of which the treatment success is increased. Once again, this can be assisted by image evaluation methods or pattern comparison methods.

Likewise, in the event of a suction loss, the chronological sequence thereof can be observed repeatedly by observing the recorded treatment video at a reduced speed. The time range of error-free laser therapy up to the time of the suction loss can be identified.

The presence of bubbles in the video image of the cornea counts as evidence of successful laser-tissue interaction (laser incision on the basis of photo disruption). Here, the creation and disappearance of the bubble pattern, and hence the observability of these bubbles during the laser therapy, depends on the applied parameters such as laser energy, pulse duration and focusing.

Thus, bubbles that only exist briefly can only be recognized with difficulty by the operator. By contrast, in the case of a high-speed recording and the subsequent observation at a reduced speed (slow-motion effect), these bubbles can also be rendered observable to the operator and they can thus obtain information about the presence of the laser therapy incision.

A particularly suitable embodiment lies in the provision of the video image in a common laser therapy system. Thus, the information obtained during the laser therapy in relation to the ablation success at different times (timestamp), which is relevant to the respective work step, can be queried by the physician during the work step of the lenticule removal.

Superimposing this information into the observation field of the observer during the lenticule removal is also advantageous.

In an example variant of the invention, prior knowledge about the expected form of the pattern, in particular a bubble pattern, produced by the interaction of the laser with the tissue is used for the automatic analysis in order to detect and assess the expected pattern by machine and hence carry this out quickly. By way of example, a search is carried out for the expected round or elliptic form of the bubble pattern in the image, and the center of the structure is measured. If the center of the structure is displaced at any point during the processing, it is possible to deduce a slip of the eye on the contact glass and the treatment can be automatically interrupted by virtue of the image evaluation device transmitting an appropriate signal to the control device.

In the development of the invention, it is not known rules that are applied but the rules are first of all established by machine by way of inductive processes. To this end, a large number of regular and irregular treatments are classified accordingly and analyzed by the image evaluation device during a supervised learning phase, or an appropriate learning pattern is supplied thereto from the outside. Subsequently, the implicitly present rule or law ascertained thus is used for automatic classification of new images. The learning pattern can also be replicated, and hence identically preconditioned systems can be produced.

In another development of the invention, the time until a critical error extent is reached is automatically estimated in the case of an automatic detection of a deviation, for example by simple extrapolation, and this is assessed in view of the expected machine processing time or time for working through a critical part of the machine processing. By way of example, if a displacement of 5 μm is detected 20 ms before completion of the incision of a lenticule surface and a displacement of 10 μm is detected 10 ms before completion of this incision, then, initially, the treatment is not interrupted but the critical incision of the lenticular surface is still completed (prediction assessment). Only then is the treatment stopped and the operator of the therapy device is requested to make an active decision about the manner of continuing. Decision criteria (e.g., in the form of parameter vectors) and limits for permitted deviations (e.g., in the form of limit value vectors) are defined, and stored in the device by the manufacturer or the operator, for the decision as to whether to continue or interrupt the machine processing. The comparison of parameter vectors or predicted parameter vectors with limit value vectors then facilitates a quick machine decision. The calculation of a predicted parameter vector can be implemented with little outlay by solving the equation of motion for the parameter vector for the time at which the critical method step will be completed. Thus, using the described example of the lenticular incision, the parameter vector is calculated on the basis of measuring its rate of change for the known time at the end of the lenticular incision. By way of the comparison of the parameter vector predicted thus with the limit value vector, there subsequently is an assessment as to whether the expected deviation can be accepted or whether there must be an immediate treatment termination. In the example described, a parameter vector of 15 μm is calculated under the assumption of a uniform movement. Assuming that the limit value vector is 20 μm in this case, no automatic treatment termination would consequently be triggered following the assessment.

In a further configuration of the invention, the therapy device can then automatically also recommend (for example on the basis of a measured parameter vector) a treatment plan that deviates from the original treatment plan (standard procedure). In the case described, an incision of an edge surface of the lenticule could be implemented with a slightly smaller diameter and a greater depth (axial extent) than originally envisaged in order thus to obtain a gap-free connection to the incision of the lenticule surface. To this end, variations in the standard procedure and their dependence on deviations are defined and stored in the device by the manufacturer or the operator.

In a further variant of the invention, the bubble pattern is not detected, but rather the contact glass edge is monitored in respect of the aspiration of connective tissue. If such a procedure is detected, all the aforementioned developments of the invention are likewise applicable. Monitoring is not restricted to the aforementioned features (bubble pattern/contact glass edge) but can also take account of other optically detectable features, which may also consider other anatomical structures of the eye (anterior chamber, lens, iris, vitreous humor, retina).

In another development of the invention, there can be a machine-based decision on the basis of measured values of a suitable detector in addition or as an alternative to the automatic optical recognition of deviations in the treatment process. To this end, at least one sensor for signal capture, a signal processing module for generating measured values and an assessment module for assessing the regularity of the measured values are required. By way of example, the measured values can be force measured values, the assessment of which serves to make a decision about the correctness of the treatment. The treatment is referred to as correct if the measured values lie in a measured value interval that is predetermined or calculated from initial values. The above-described principle of prediction assessment can likewise find use in this case.

The effect of the invention in view of solving the problem lies in the faster reaction of the automated monitoring system in relation to purely manual monitoring by the operator. In order to obtain a significant improvement in relation to the human reaction time of at least 200 ms to 500 ms, a machine reaction time of less than 200 ms, for example less than 100 ms is advantageous.

The accuracy of the recognition of a deviation also plays a role for the speed of the reaction. A suction loss often starts with the eye slowly slipping off the contact glass/patient interface. Recognizing even small errors in this case, firstly, facilitates a fast reaction and, secondly, also facilitates having sufficient time to estimate the development over time and assess the process (prediction assessment). Provision is made for the accuracy of the error recognition by the image processing to be better than 50 μm; for example, it is less than 20 μm and only 5 μm in the best case. What follows in relation to an observation field with an extent of at least 11 mm is an example pixel count for the image recording device of greater than or equal to 2200×2200, in a further example greater than or equal to 4000×4000.

It is understood that the features specified above and the features yet to be explained below can be used not only in the specified combinations, but also in other combinations or on their own, without departing from the scope of the present invention.

BRIEF DESCRIPTION OF THE DRAWINGS

The invention is explained in even greater detail below for example with reference to the accompanying drawings, which also disclose features essential to the invention. In the drawings.

DETAILED DESCRIPTION

Figure 1:
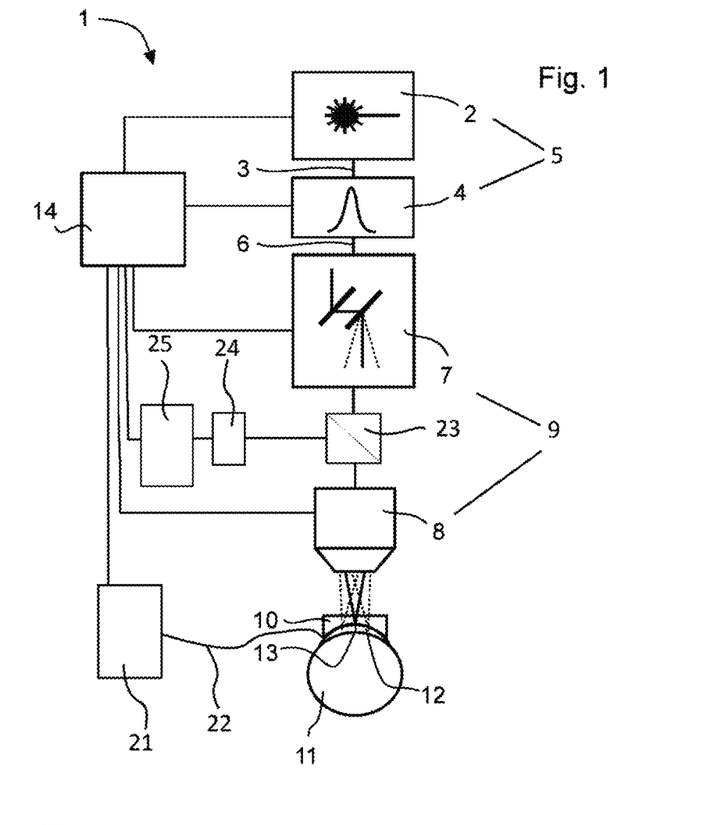
FIG. 1 depicts a schematic illustration of an apparatus for performing incisions in the interior of the eye, in the cornea in this case.

FIG. 1 depicts, in an example and schematic fashion, an apparatus 1 for performing a lenticule-extracting refractive error correction. The apparatus 1 comprises a laser 2 which provides pulsed laser radiation, wherein the laser 2 of the embodiment explained emits a pulsed raw beam 3 at a wavelength which penetrates into the tissue of the cornea such that there can be processing there by nonlinear effects. The raw beam 3 is formed with respect to the pulse duration by a pulse shaper 4, wherein there can be a predistortion known from the prior art, the latter ensuring that, after passing through the further optical path of the beam path in the material, i.e., in the cornea of the eye, the desired pulse length of, e.g., ≤1 ps is present Together, the pulse shaper 4 and the laser 2 form a laser beam source 5, which emits a pulsed laser beam 6 with the desired pulse length.

The pulsed laser beam 6 further passes through a scanner 7, which for example brings about a two-dimensional deflection across the direction of propagation of the laser radiation. The laser beam 6 scanned in this way is focused into the cornea by an objective lens 8. Together with the objective lens 8, the scanner 7 forms a beam shaping device 9, which ensures that the pulsed laser radiation 6 is focused at adjustable locations within a cornea of an eye, with the focal diameter being less than 3 µm there.

Optionally, the laser beam source 5 can comprise a so-called pulse picker, which may be a constituent part of the pulse shaper 4, for example. This pulse picker alters the raw beam 3 in respect of the frequency of the laser radiation pulses which have a processing effect in the cornea. By way of example, it is possible to embody the laser 2 in such a way that it provides a raw beam 3 at a pulse frequency that is significantly higher than the pulse frequency desired for the laser pulses of the laser beam 6 that are effective in terms of the processing. The pulse picker then reduces the frequency of the effective laser radiation pulses by virtue of rendering individual laser radiation pulses harmless in respect of their processing effect. By way of example, this can be implemented by virtue of the pulse picker increasing the pulsed length. The significance of the pulse picker, which is known in the prior art, will still be explained in more detail below on the basis of FIG. 3.

In the embodiment shown in FIG. 1, the pulse frequency of the pulsed laser beam 6 is between 1.2 MHz and 10 MHz, with the frequency relating to those pulses that have a processing effect, i.e., the pulses that were not rendered harmless by a possibly present pulse picker.

The energy of these pulses of the pulsed laser beam 6 is between 1 nJ and 200 nJ, for example between 10 nJ and 100 nJ, in another example between 20 nJ and 80 nJ.

The wavelength of the laser beam 6 lies in a range of 1030 nm to 1060 nm or in any other spectral range that can penetrate into the cornea, i.e., for which the cornea has a transmittance of for example at least 0.8.

The apparatus 1 further comprises a contact glass 10, which is used to fixate the eye 11 and also to impart a desired and known shape to the surface of the cornea 12 of the eye 11. To this end, the corresponding contact face of the contact glass 10 has a radius of curvature of 50 mm or less, for example 20 mm or less. The contact glass 10 is drawn against the cornea 12 of the eye 11 by application of negative pressure provided by a negative pressure production device 21, which is connected via a negative pressure line 22 to the contact glass 10. In this case, the contact glass 10 can be embodied as presented in WO 2007/022993, for example.

The objective lens 8 focuses the laser radiation 6 at a focus 13, which is located within the cornea 12. The focus 13 for example has a maximum diameter of 3 µm, in another example of no more than 2 µm.

Using dashed lines, FIG. 1 shows that the focus 13 is located at different points in the cornea 12 of the eye 11, depending on the effect of the scanner 7. In the structure of FIG. 1, the scanner 7 brings about a deflection transversely to the principal direction of incidence of the laser radiation 6. An adjustment of the focal position along the principal direction of incidence is implemented by suitable control of the objective lens 8, which has a suitable embodiment for a z-adjustment.

A beam splitter 23 which serves to pass the laser radiation 6 and image an image of the cornea 12 on a camera 24 (possibly via optics not illustrated here) is arranged at a suitable point (in this case between scanner 7 and objective lens 8). The camera 24 is connected to an image evaluation device 25 which in turn is connected to the control device 14. Alternatively, the camera 24 can also be arranged outside of the beam path of the laser 2; what is important is that it can record an image of the eye or the cornea in a suitable spectral range. To this end, it is for example sensitive in the near infrared but can also be set up to be sensitive in the visual spectral range.

The laser beam source 5 (realized by the laser 2 and pulse shaper 4 in the structure of FIG. 1) and the beam shaping device 9 (realized by the scanner 7 and objective lens 8 in the structure of FIG. 1) are connected via control lines, not provided with a reference sign, to a controller 14 which suitably controls these elements. By way of the control, the controller 14 produces a cut surface in the cornea. The corresponding relationships are illustrated in a sectional illustration in FIG. 2, which schematically shows the cornea 12.

A lenticule 15 is isolated in the cornea 12 by adjusting the focus 13 of the pulsed laser radiation 6. The lenticule 15 is delimited by a flap surface 16 on the anterior side and by a lenticule surface 17 on the posterior side. To keep the boundaries of the lenticule 15 as simple as possible, the flap surface 16 is at a constant distance from the front surface 18 of the cornea 12. Consequently, the flap surface 16 is not curved in relation to the front surface 18. This is different in the case of the lenticule surface 17, which is curved in relation to the front surface 18. Without such curvature, the removal of the lenticule 15 would not sufficiently change the curvature of the front surface 18 of the cornea 12. By contrast, the lenticule surface 17 that is curved in relation to the front surface 18 already sets a clinically relevant change in the curvature of the front surface 18 of the cornea 12 when the lenticule 15 is removed, even in the case of a small tissue volume. This removal is implemented by way of a lateral incision not illustrated in FIG. 2, which, for example, leads from the flap surface 16 to the front surface 18 at the edge of the lenticule 15 and which allows the isolated lenticule 15 to be extracted, possibly after a preceding comminution of the material of the lenticule 15. The flap surface 16 and the lenticule surface 17 are symmetric with respect to the optical axis OA in the illustration of FIG. 2. This occurs automatically for the flap surface 16 if it has a constant distance from the front surface 18.

Figure 2:
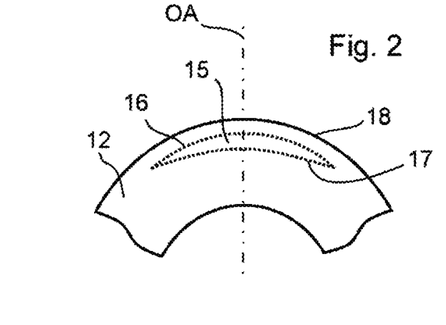
FIG. 2 depicts a simplified sectional illustration through the cornea for elucidating an incision.

In addition to the flap surface 16 and the lenticule surface 17, the boundaries of the lenticule 15 can naturally comprise even more surfaces. By way of example, in the case of a lenticule 15 that is thinner at the optical axis OA than at regions distant from the axis, provision can be made for an additional edge surface which connects the flap surface 16 to the lenticule surface 17, the latter then having a more strongly curved profile than the flap surface 16 and the front surface 18.

Figure 3:
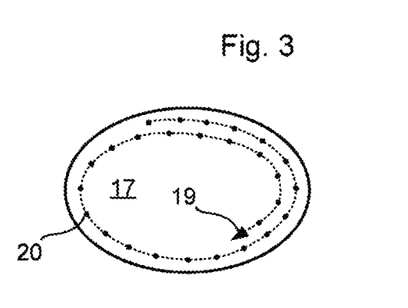
FIG. 3 depicts a projection of the cut surface as the image recording device records the cut surface generation.

The cut faces for isolating the lenticule 15 are produced by virtue of the focus 13 being displaced along a trajectory which is located in the corresponding surface. This is shown in an example fashion in FIG. 3 on the basis of the lenticule surface 17, which is elliptical here for reasons of clarity. This should indicate that the apparatus 1 can be used to correct not only a spherical visual defect but also an astigmatism. When correcting higher order aberrations, the lenticule 15 is no longer rotationally symmetric with respect to the optical axis OA in all cases. FIG. 3 shows the lenticule surface 17 folded open in the plane of the drawing. A trajectory 19 is shown in FIG. 3 using dashed lines. The position of the focus 13 is adjusted along this trajectory. Naturally, as a rule, it is necessary here not only to carry out an adjustment transversely to the optical axis OA but also an adjustment of the focal position along the optical axis OA. This cannot be recognized in FIG. 3 because this figure shows the lenticule surface 17 folded open in the plane of the drawing, which is why the trajectory 19 lies in a plane in the illustration of FIG. 3. If the section through the lenticule 15 in FIG. 2 is considered, it becomes clear that the z-position of the focus is also displaced away from the front surface 18 with increasing distance from the optical axis OA.

Target points 20 are plotted along the spiral trajectory 19 of FIG. 3, which essentially describes contour lines. They each denote a point at which a laser pulse of the pulsed laser radiation 6 is delivered. By stringing together the target points 20 along the trajectory 19 and by suitably choosing the trajectory 19, the lenticule surface 17 overall is embodied as a cut surface. Here, the distances between the target points 20 are chosen in such a way that, where possible, no material bridges remain; thus, the lenticule surface 17 is generated as a cut surface over the entire area thereof.

On the basis of FIG. 3 it is easy to understand why it is advantageous to render the pulse frequency of the pulsed laser beam 6 changeable. If the intention is to arrange the target points 20 as equidistantly as possible, the pulse frequency and the displacement speed of the beam shaping device 9 should be matched to one another. Since a laser 2 at high pulse frequency is generally only adjustable with much effort, it is advantageous to initially provide a raw beam 3 with the laser 2, said raw beam having a pulse frequency that is greater than or equal to the maximum pulse frequency desired for the laser beam 6. It may be easier to realize such a laser 2 and combine the latter with a pulse picker than construct a laser that is directly adjustable in respect of its pulse frequency. Thus, the pulse frequency can be matched to the displacement speed and the cut surface generation duration is minimized by reducing the number of processing points. Hence, there can also be a change in the target image of the pattern of the target points 20 or the target image of the effects caused thereby in the material (bubble pattern), which the image evaluation device 25 can compare with the current image of the camera 24.

The control device 14 in FIG. 1 contains the system for storing the video images registered with the camera 24 and the image evaluation device 25. Here, the control device 14 also contains the system for reproducing the video sequences at a reduced speed (digital video recorder with a slow-motion function). In conjunction with the image evaluation device 25, relevant features such as bubble formation and bubble breakdown and features regarding the progression of suction loss incidents are reproduced at a video speed that is observable by the physician.

When included in the entire treatment progress, the control device 14 allows the reproduction of selected images which are adapted to the respective treatment situation by using timestamps.

As a result, the control device facilitates the targeted jump to video images at relevant times of the previously registered laser therapy and the superimposition of this information into the observation field of the physician, in particular during the subsequent lenticule removal.

Figure 4:
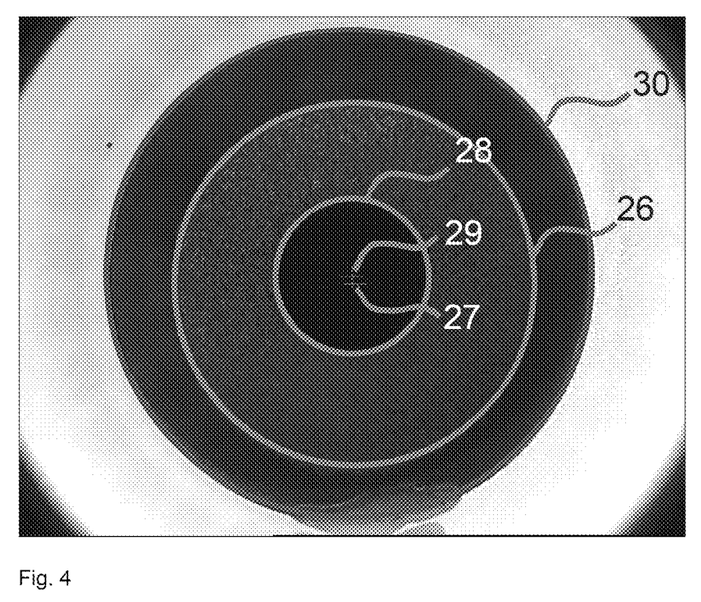
FIG. 4 depicts a first example for evaluating a recording of the cut surface generation.

FIG. 4 is used to explain embodiments of the invention in more detail using the example of a release of or reduction in the vacuum fixation of the patient's eye ("suction loss") as a result of aspiration of connective tissue (lower image edge). The eye 11 with the contact glass 10, as recorded by the camera 24, is illustrated. The incision in the cornea is implemented along a trajectory 19 extending from the outside to the inside. By way of image processing, the image evaluation device 25 determines the outer edge 26 of the incision or sectional image and the center 27 thereof. The inner edge 28 of the incision and its center 29 (actual image parameter) is determined continuously during the treatment. A displacement of the center 29 of the inner edge 28 in relation to the center 27 (target image parameter) of the outer edge 26 of the incision indicates that the eye 11 has moved under the contact glass 10 and hence that the fixation of the eye is no longer stable. By way of the control device 14, it is possible to provide the operator with an appropriate signal or else automatically terminate the treatment if the lateral displacement (parameter vector) of the patient's eye has exceeded a predefined critical error limit (limit value vector). According to the invention, this information can be expanded by a prediction of the parameter vector and the decision to terminate can then be made exclusively or additionally on the basis of the prediction. The edge 30 of the contact glass 10 would also be available as further information. The extent to which the incision has been worked through can be deduced from the diameter of the inner edge 28 and, if the incision has been largely completed, the image evaluation device can also decide that continuing the incision is preferable to a termination.

Figure 5:
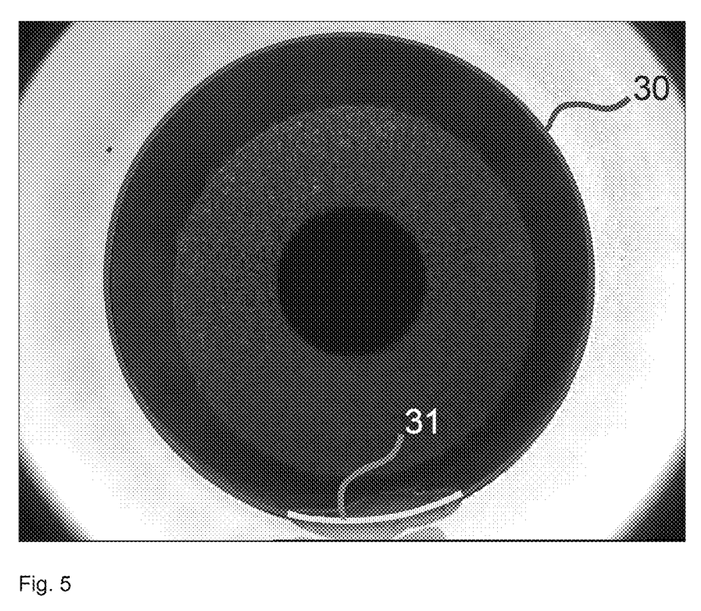
FIG. 5 depicts a second example for evaluating a recording of the cut surface generation.

FIG. 5 depicts, in an example fashion, an alternative evaluation process for the image of the camera. In this case, the image of the edge 30 of the contact glass 10 is assessed. In this case, the aspiration of connective tissue in the region 31 is automatically detected and assessed. In that case, the parameter vector would be, for example, the arc length of the edge affected by the connective tissueexe aspiration. By way of example, if the parameter vector exceeds a predetermined limit value (limit vector), the control device 14 is provided with a signal. The latter can then terminate the treatment or provide the operator with a signal or a treatment recommendation. In the example shown in FIG. 5, a prediction for the further development of the disrupting process (aspiration of the conjunctiva) over time can also be derived by capturing the time profile of the change. In this case, the assessment is implemented not only on the basis of the current extent of the disruption but also includes the prediction of its time profile (multidimensional parameter vector) in relation to the time required for the completion of the treatment or the current treatment step.

While the invention has been presented in detail in the drawings and the description above, the illustration and description should be considered illustrative or exemplary in nature and not restrictive. It is understood that changes and modifications can be undertaken within the scope of the following claims by a person skilled in the art. In particular, the present invention comprises further embodiments with any combination of features of embodiments described above or below.

The invention claimed is:

1. An apparatus for producing incisions in an interior of an eye, comprising:

a laser beam source embodied to emit pulsed laser radiation in a femtosecond range at a wavelength penetrating the cornea into the interior of the eye, with a beam shaping device which has an image field and which focuses the pulsed laser radiation into the interior of an eye at a focus located within the image field, and which displaces the focus within the image field, a control device that controls the laser beam source and the beam shaping device in order to produce at least one incision in the interior of the eye by specifying a trajectory, an image recording device embodied to record at least part of the image field, and an image evaluation device that evaluates recordings of the image recording device and produces signals directed to the control device, an operator or both;

wherein the image evaluation device determines at least one parameter vector of lateral displacement of the eye and compares the at least one parameter vector to a limit value vector representing a predefined critical error limit and determines at least one prediction for the at least one parameter vector and compares said at least one prediction to the limit value vector.

2. The apparatus as claimed in claim 1, wherein the laser beam source emits pulsed laser radiation with a pulse frequency of 1.2 MHz to 10 MHz.

3. The apparatus as claimed in claim 1, wherein the laser beam source emits the pulsed laser radiation with a pulse energy of 1 nJ to 100 nJ.

4. The apparatus as claimed in claim 1, wherein the focus has a maximum diameter of less than 3 μm.

5. The apparatus as claimed in claim 1, wherein the laser beam source emits the pulsed laser radiation at a wavelength of 1030 nm to 1060 nm.

6. The apparatus as claimed in claim 1, wherein the laser beam source emits the pulsed laser radiation with a pulse length of less than 1 ps.

7. A method for producing incisions in an interior of an eye, comprising:

defining at least one cut surface in the interior of the eye, defining a trajectory located in the cut surface, emitting pulsed laser radiation in a femtosecond range at a wavelength penetrating the cornea into the interior of the eye, using a beam shaping device, which has an image field and which focuses the pulsed laser radiation into the interior of the eye at a focus located within the image field, displacing the focus in the interior of the eye and within the image field, using an image recording device to record at least part of the image field, evaluating images recorded by the image recording device by operation of an image evaluation device and producing signals directed to the control device, the operator or both; and determining by operation of the image evaluation device at least one parameter vector of lateral displacement of the eye and comparing the at least one parameter vector to a limit value vector representing a predefined critical error limit and determining at least one prediction for the at least one parameter vector and comparing said at least one prediction to the limit value vector.

8. The method as claimed in claim 7, further comprising evaluating the images from the image recording device by application of the image evaluation device by image recognition or image measurement.

9. The method as claimed in claim 7, wherein the image evaluation device is configured to recognize a movement of the eye.

10. A computer program product containing program instructions which, when executed on one or more computers realize the method as claimed in claim 7, wherein the one or more computers are operably coupled to the laser emitting pulsed laser radiation in a femtosecond range at a wavelength penetrating the cornea into the interior of the eye, the beam shaping device, the image recording device and the image evaluation unit.

11. A computer program product containing program instructions which, when executed on one or more computers realize the method as claimed in claim 8, wherein the one or more computers are operably coupled to the laser emitting pulsed laser radiation in a femtosecond range at a wavelength penetrating the cornea into the interior of the eye, the beam shaping device, the image recording device and the image evaluation unit.

12. A computer program product containing program instructions which, when executed on one or more computers realize the method as claimed in claim 9, wherein the one or more computers are operably coupled to the laser emitting pulsed laser radiation in a femtosecond range at a wavelength penetrating the cornea into the interior of the eye, the beam shaping device, the image recording device and the image evaluation unit.

* * * * *

UNITED STATES PATENT AND TRADEMARK OFFICE
CERTIFICATE OF CORRECTION

PATENT NO. : 12,251,339 B2
APPLICATION NO. : 17/278312
DATED : March 18, 2025
INVENTOR(S) : Bischoff et al.

Page 1 of 1

It is certified that error appears in the above-identified patent and that said Letters Patent is hereby corrected as shown below:

In the Specification

Column 4, Line 33, delete "comprising" and insert --comprising:--

Column 5, Line 64, delete "n example" and insert --an example--

Column 9, Line 2, delete "there by" and insert --thereby--

Column 12, Line 41, delete "tissueexe" and insert --tissue--

Signed and Sealed this
Thirteenth Day of May, 2025

Coke Morgan Stewart
*Acting Director of the United States Patent and Trademark Office*